(12) United States Patent
Hardman et al.

(10) Patent No.: US 9,186,146 B2
(45) Date of Patent: Nov. 17, 2015

(54) SYSTEM AND METHOD FOR MECHANICAL CLOSURE OF WOUNDS

(71) Applicant: KCI Licensing, Inc., San Antonio, TX (US)

(72) Inventors: Ian Hardman, Bournemouth (GB); Colin Hall, Poole (GB); James Sealy, New Milton (GB)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 14/229,508

(22) Filed: Mar. 28, 2014

(65) Prior Publication Data

US 2014/0213994 A1    Jul. 31, 2014

Related U.S. Application Data

(62) Division of application No. 12/326,589, filed on Dec. 2, 2008, now Pat. No. 8,721,629.

(51) Int. Cl.
| | |
|---|---|
| *A61M 27/00* | (2006.01) |
| *A61B 17/08* | (2006.01) |
| *A61M 1/00* | (2006.01) |
| *A61B 17/00* | (2006.01) |
| *A61B 17/30* | (2006.01) |

(52) U.S. Cl.
CPC ............ *A61B 17/085* (2013.01); *A61M 1/0088* (2013.01); *A61B 2017/00561* (2013.01); *A61B 2017/081* (2013.01); *A61B 2017/086* (2013.01); *A61B 2017/308* (2013.01)

(58) Field of Classification Search
CPC ................. A61B 17/085; A61B 2017/00561; A61B 2017/081; A61B 2017/086; A61B 2017/308; A61M 1/0088
USPC ............ 604/8–10, 19–21, 35, 290, 216, 313, 604/543; 606/215–218
See application file for complete search history.

(56) References Cited

U.S. PATENT DOCUMENTS

| | | |
|---|---|---|
| 3,874,387 A | 4/1975 | Barbieri |
| 4,233,969 A | 11/1980 | Lock et al. |
| 4,373,519 A | 2/1983 | Errede et al. |
| 4,569,348 A | 2/1986 | Hasslinger |
| 5,149,331 A | 9/1992 | Ferdman et al. |
| 5,263,971 A | 11/1993 | Hirshowitz et al. |
| 5,298,015 A | 3/1994 | Komatsuzaki et al. |
| 352,356 A | 11/1994 | Hirshowitz et al. |
| 360,463 A | 7/1995 | Steiner et al. |

(Continued)

FOREIGN PATENT DOCUMENTS

| | | |
|---|---|---|
| WO | WO-99/01173 A1 | 1/1999 |
| WO | WO-2007/092397 A2 | 8/2007 |

OTHER PUBLICATIONS

Argenta, L.C. et al. "Vacuum-Assisted Closure: A New Method for Wound Control and Treatment: Clinical Experience" Annals of Plastic Surgery, vol. 38, No. 6, Jun. 1997; pp. 563-577.

(Continued)

*Primary Examiner* — Philip R Wiest
(74) *Attorney, Agent, or Firm* — McCarter & English, LLP; Matthew R. Van Eman

(57) ABSTRACT

Devices for treating wounds and methods of treating wounds are described. In use, the devices allow both mechanical force and negative pressure therapy.

28 Claims, 15 Drawing Sheets

(56) References Cited

U.S. PATENT DOCUMENTS

| | | |
|---|---|---|
| 5,437,651 A | 8/1995 | Todd et al. |
| 5,441,540 A | 8/1995 | Kim |
| 5,507,775 A | 4/1996 | Ger et al. |
| 5,531,790 A | 7/1996 | Frechet et al. |
| 5,549,584 A | 8/1996 | Gross |
| 5,549,713 A | 8/1996 | Kim |
| 5,618,310 A | 4/1997 | Ger et al. |
| 5,636,643 A | 6/1997 | Argenta et al. |
| 5,645,081 A | 7/1997 | Argenta et al. |
| 5,649,960 A * | 7/1997 | Pavletic ............... 606/216 |
| 5,662,714 A | 9/1997 | Charvin et al. |
| 5,733,305 A | 3/1998 | Fleischmann |
| 5,814,067 A | 9/1998 | Fleischmann |
| 5,895,413 A | 4/1999 | Nordstrom |
| 5,928,265 A | 7/1999 | Fleischmann |
| 5,968,097 A | 10/1999 | Frechet et al. |
| 5,972,022 A | 10/1999 | Huxel |
| 6,010,524 A | 1/2000 | Fleischmann |
| 6,071,267 A | 6/2000 | Zamierowski |
| 6,135,116 A | 10/2000 | Vogel et al. |
| 6,345,623 B1 | 2/2002 | Heaton et al. |
| 6,494,896 B1 | 12/2002 | D'Alessio et al. |
| 6,553,998 B2 | 4/2003 | Heaton et al. |
| 6,814,079 B2 | 11/2004 | Heaton et al. |
| 7,198,046 B1 | 4/2007 | Argenta et al. |
| 7,208,006 B2 | 4/2007 | Fleischmann |
| 7,361,185 B2 | 4/2008 | O'Malley et al. |
| 2002/0120185 A1 | 8/2002 | Johnson |
| 2003/0092969 A1 | 5/2003 | O'Malley et al. |
| 2004/0073151 A1 | 4/2004 | Weston |
| 2004/0122434 A1 | 6/2004 | Argenta et al. |
| 2004/0267309 A1 | 12/2004 | Garvin |
| 2006/0058842 A1 | 3/2006 | Wilke et al. |
| 2007/0219471 A1 | 9/2007 | Johnson et al. |
| 2007/0219512 A1 | 9/2007 | Heaton et al. |
| 2008/0108977 A1 | 5/2008 | Heaton et al. |
| 2010/0030260 A1 | 2/2010 | Fleischmann |
| 2011/0238110 A1 * | 9/2011 | Wilke et al. ............... 606/216 |

OTHER PUBLICATIONS

Blackburn II, J.H. et al. "Negative-Pressure Dressings as a Bolster for Skin Grafts" Annals of Plastic Surgery, vol. 40, No. 5, May 1998, pp. 453-457.

Chariker, M.E. et al. "Effective management of incisional and cutaneous fistulae with closed suction wound drainage" Contemporary Surgery, vol. 34, Jun. 1989, pp. 59-63.

Chinn, S.D. et al. "Closed Wound Suction Drainage" The Journal of Foot Surgery, vol. 24, No. 1, 1985; pp. 76-81.

Dattilo Jr., P.P. et al. "Medical Textiles: Application of an Absorbable Barbed Bi-directional Surgical Suture" Journal of Textile and Apparel, Technology and Management, vol. 2, Issue 2, Spring 2002, pp. 1-5.

Defranzo, A.J. et al. "Vacuum-Assisted Closure for the Treatment of Abdominal Wounds" Clinics in Plastic Surgery, vol. 33, No. 2, Apr. 2006, pp. 213-224.

Flack, S. et al. "An economic evaluation of VAC therapy compared with wound dressings in the treatment of diabetic foot ulcers" J. Wound Care, vol. 17, No. 2, Feb. 2008, pp. 71-78.

KCI Licensing, Inc. "V.A.C.® Therapy Safety Information" 2007, pp. 1-4.

Masters, J. "Reliable, Inexpensive and Simple Suction Dressings" Letters to the Editor, British Journal of Plastic Surgery, vol. 51, No. 3, 1998, p. 267.

O'Connor, J. et al. "Vacuum-Assisted Closure for the Treatment of Complex Chest Wounds" Ann. Thorac. Surg., vol. 79, 2005, pp. 1196-1200.

* cited by examiner

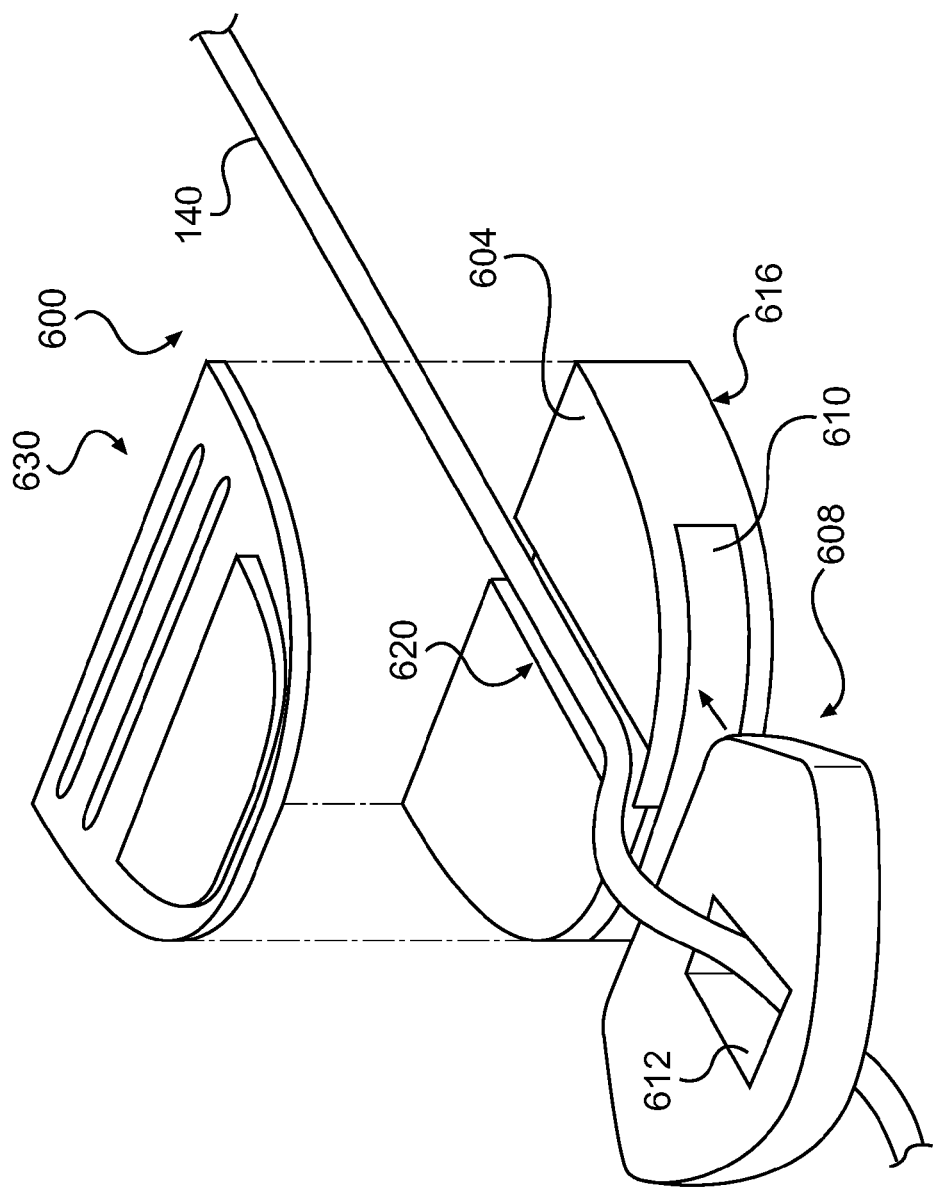

SYSTEM AND METHOD FOR MECHANICAL CLOSURE OF WOUNDS

This application is a divisional application of U.S. Utility application Ser. No. 12/326,589, filed on Dec. 2, 2008 all of which is incorporated herein by reference in its entirety.

BACKGROUND

Reduced pressure, or vacuum-assisted, therapies can be effective for improving wound healing due to a variety of different causes and at a number of different anatomical locations. Typically, reduced pressure therapies include a porous material that is placed at a wound site. A membrane or drape is placed over the porous material to provide an airtight seal at the wound area, and a negative pressure is applied to the porous material to provide a reduced pressure at the wound site.

Tissue stretching systems can assist with wound closure. Such stretching systems may provide mechanical forces to tissue around the wound to allow approximation of the wound margins over time.

SUMMARY

According to certain embodiments, a wound treatment device is provided that comprises a first body comprising at least one first opening configured for attachment to a reduced pressure source and at least one fluid passage extending at least partially through the first body and in fluid communication with the at least one opening. The device further comprises two or more elongated sections, each attached to the first body, extending from the first body in different directions, and having a length that is adjustable with respect to the first body.

According to certain embodiments, a method for treating a wound is provided that comprises mechanically coupling two or more elongated sections to tissue at two or more locations around a wound, the two or more elongated sections being attached to a first body comprising at least one first opening configured for attachment to a reduced pressure source and at least one fluid passage extending at least partially through the first body and in fluid communication with the at least one opening. The method further comprises creating tension in the two or more elongated sections to pull the tissue at the two or more locations around the wound closer together.

According to certain embodiments, a wound treatment device is provided that comprises a first body having a substantially rigid material body. The device further comprises two or more elongated sections, each attached to the first body, extending from the first body in different directions, and having a length that is adjustable with respect to the first body. The device also comprises an adhesive for mechanically coupling two or more connectors, each attached to one of the two or more elongated sections, to tissue surrounding a wound.

According to certain embodiments, a method for treating a wound is provided that comprises mechanically coupling two or more elongated sections to tissue at two or more locations around a wound using an adhesive, the two or more elongated sections being attached to a first material body. The method further comprises creating tension in the two or more elongated sections to pull the tissue at the two or more locations around the wound closer together.

DESCRIPTION OF THE DRAWINGS

FIG. 6A illustrates another adjustable connector attached to an elongated section of a wound treatment device, according to certain exemplary embodiments.

DESCRIPTION OF CERTAIN EXEMPLARY EMBODIMENTS

Figure 1:
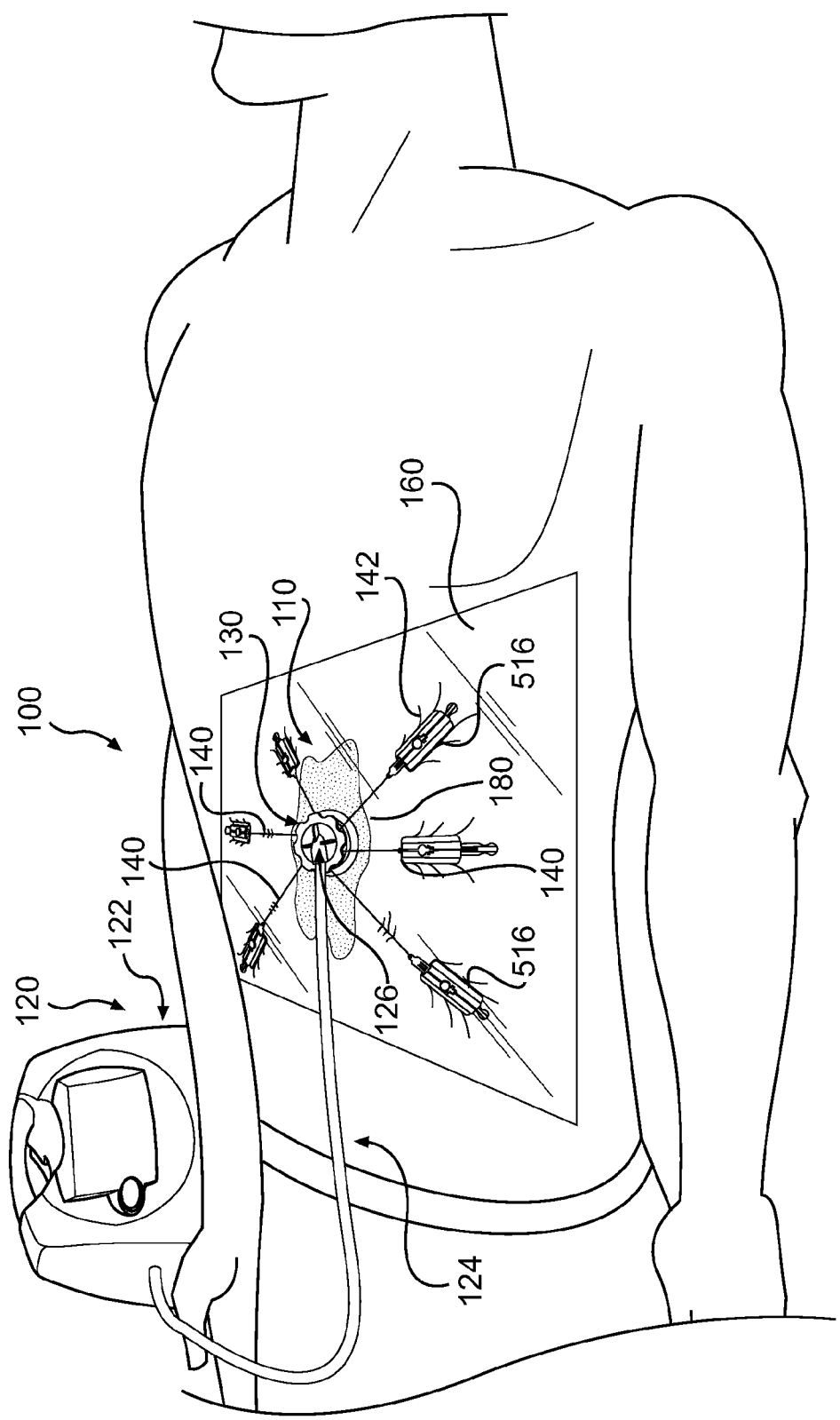
FIG. 1 illustrates a wound treatment device, which provides mechanical force and reduced pressure therapy, according to certain exemplary embodiments.

Reference will now be made in detail to the certain exemplary embodiments according to the present disclosure, certain examples of which are illustrated in the accompanying drawings. Wherever possible, the same reference numbers will be used throughout the drawings to refer to the same or like parts.

The present disclosure pertains to wound treatment devices that can be used to provide mechanical forces to assist in closing, or at least partially closing, wounds. In some embodiments, the devices of the present disclosure can be configured to provide mechanical forces directed at approximating wound margins without damaging surrounding skin or other tissue. In some embodiments, the mechanical forces are applied without penetrating skin or other tissue. In certain embodiments, the devices provide mechanical forces directed at approximating wound margins in conjunction with reduced pressure therapy. In various embodiments, the devices can be used to treat a variety of different wound shapes and at many different anatomical locations.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit, unless specifically stated otherwise. Also the use of the term "portion" may include part of a moiety or the entire moiety.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The term "reduced pressure," as used herein, generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure of tissue at the tissue site. Reduced pressure may initially generate fluid flow in the tube and the area of the tissue site. As the hydrostatic pressure around the tissue site approaches the desired reduced pressure, the flow may subside, and the reduced pressure is then maintained. Unless otherwise indicated, values of pressure stated herein are gage pressures.

The term "fluid" as used herein generally refers to a gas or liquid, but may also include any other flowable material, including but not limited to gels, colloids, and foams.

Although reduced pressure therapy is effective to improve healing times and reduce complications for many types of wounds, in some cases, additional therapies may help improve results. For example, for larger wounds, there may be insufficient overlying dermal, epidermal, and/or subcutaneous tissue to cover the entire wound. In such cases, skin grafts or other reconstructive procedures may be used to cover the wound. In certain embodiments, devices described herein can be used to provide mechanical forces and reduced pressure therapy to assist in wound closure, resulting in wound closure and healing without grafting or other reconstructive procedures. In certain embodiments, devices described herein can be used to provide mechanical forces and reduced pressure therapy to assist in wound closure, and may be used before, simultaneously with, and/or after grafting or other procedures or therapies.

In some embodiments, the devices described herein can be used to assist in treating wounds caused by trauma due to injury and/or surgery. In addition, some surgical wounds are closed using delayed primary closure or closure by secondary approximation. In certain embodiments, devices described herein can be used to provide mechanical forces and reduced pressure therapy to assist in wound closure by delayed primary closure or by secondary approximation. Further, certain wounds are caused by diseases such as diabetes or vascular disease, and may not be due to surgery or trauma. In certain embodiments, the devices described herein may be used to assist in healing of wounds caused by any disease.

Many mechanical wound closure systems include sharp hooks or barbs to grasp the tissue adjacent to the wound. These hooks and barbs may be effective for short-term application of mechanical forces to the surrounding tissues, but, when used over more extended times, can cause the adjacent tissue to break down. In certain embodiments, the devices described herein are able to attach to tissue without hooks or barbs.

In addition, prior mechanical wound closure devices are not compatible for use with reduced pressure therapy devices. The devices described herein are compatible with reduced pressure therapy. In certain embodiments, the devices disclosed herein allow for periodic replacement of the porous material or other procedures used in reduced pressure therapy.

Figure 2:
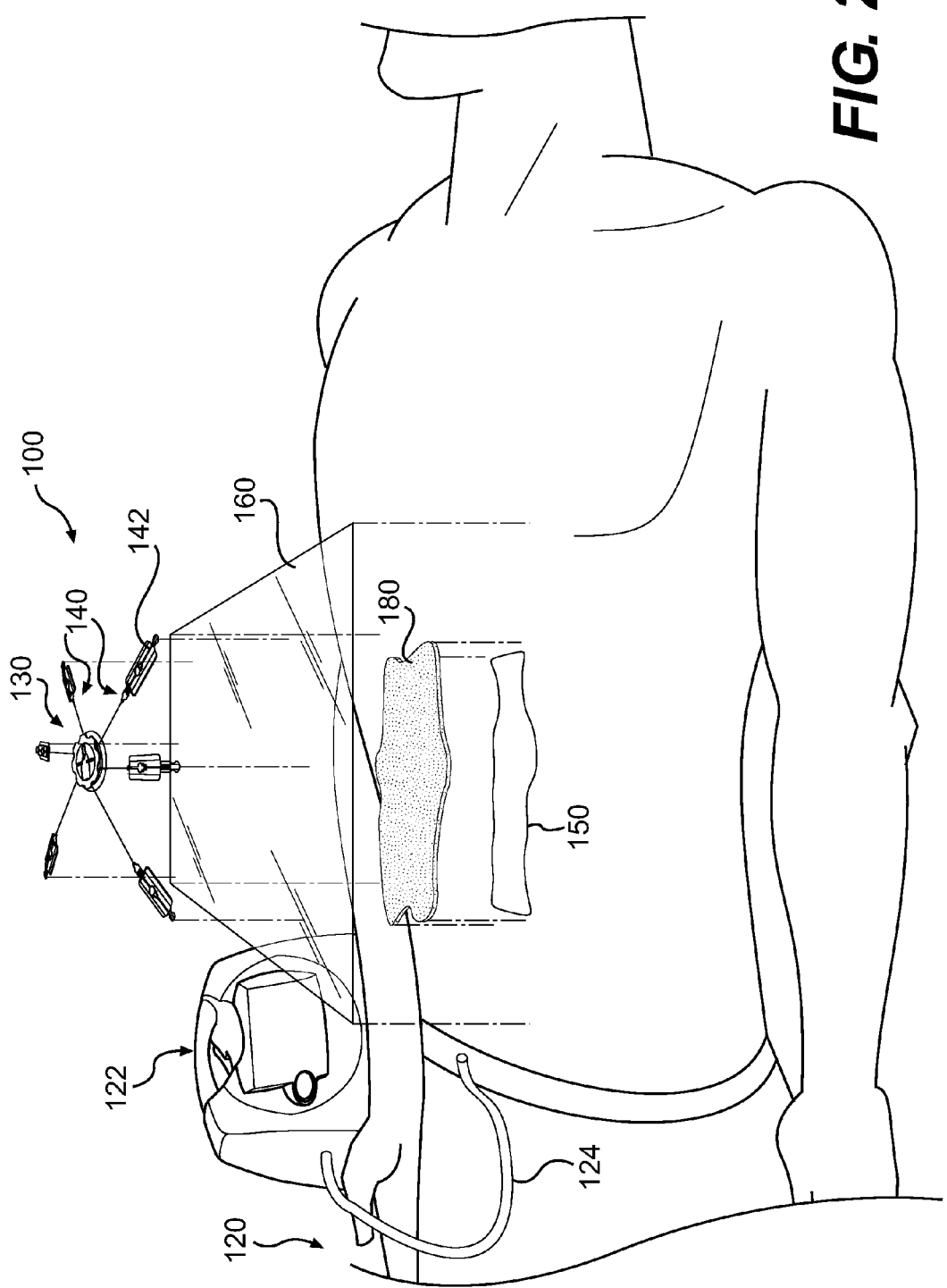
FIG. 2 illustrates an exploded view of the device of FIG. 1.

FIG. 1 illustrates a wound treatment device 100, including a mechanical treatment device 110 and reduced pressure therapy device 120, according to certain exemplary embodiments, and FIG. 2 illustrates an expanded view of the device 100 of FIG. 1, indicating how the components may be applied to a patient in certain embodiments. As shown and described in more detail below, the mechanical treatment device 110 includes a first body 130 and two or more elongated sections 140 attached to and extending from the first body 130. The elongated sections 140 are configured to be attached to tissue around a wound or to a flexible sheet 160 overlying the wound and attached to tissue around the wound. The elongated sections 140 can be positioned to provide forces directed at pulling the wound margins together, and the forces can be controlled by adjusting the length of the elongated sections 140 using a tightening mechanism of the first body 130.

Further, in some embodiments, the device 100 can include a reduced pressure therapy device 120. As shown, the reduced pressure therapy device 120 can include a pump 122 fluidly connected to the mechanical treatment device 110, e.g., through a fluid passage or tubing 124. In some embodiments, the first body 130 of the mechanical treatment device 110 can include a fluid or suction connector 126 configured to be coupled with the fluid passage or tubing 124. The connector 126 can be fluidly coupled with the space underlying the first body 130, thereby providing suction or reduced pressure to the wound site. Accordingly, the first body 130 can provide a fluid connection between the fluid passage 124 and the wound site. As noted, in some embodiments, the mechanical treatment device 110 can be designed to allow adjustable mechanical forces to be applied to tissue surrounding wounds, while allowing reduced pressure therapy to be administered.

The mechanical treatment device 110 can provide tension to wound margins for a variety of different wound shapes and at various anatomical sites. For example, as shown in FIGS. 1 and 2, the device 110 includes six elongated sections 140 extending on substantially opposite sides of an elongated, or substantially linear wound site 150 (labeled in FIG. 2). As shown in FIGS. 1 and 2, the elongated sections 140 can be formed from a flexible material, such as a wire, cord, or string, attached to a distal connector 142, which is configured to engage tissue (e.g., skin) or a flexible sheet 160 overlying the wound site 150. In some embodiments, the elongated sections can be formed from elastic or flexible polymeric materials.

As noted, FIG. 1 illustrates a mechanical treatment device 110 including six elongated sections 140, but the number of elongated sections 140 can be varied. In certain embodiments, the number of elongated sections 140 may relate to the intended use, the shape or size of the wound to be treated, and/or the anatomical site of the wound. In some embodiments, the mechanical treatment device 110 will include at least two elongated sections, at least three elongated sections, at least four elongated sections, at least five elongated sections, at least six elongated sections, at least seven elongated sections, or at least eight elongated sections. In various embodiments, any suitable number of elongated sections can be selected based on the specific wound to be treated.

In addition, in various embodiments, the orientation and/or length of the elongated sections 140 can be varied. In certain embodiments, the orientation and/or length is based on the specific wound to be treated. For example, as shown in FIG. 1, three elongated sections are placed on each side of an elongated wound, thereby allowing the wound edges to be pulled towards one another. However, as few as two elongated sections 140 can be used, each being disposed on opposite sites of a wound to pull the wound margins towards one another.

In certain embodiments, for more round and/or irregular wounds, the orientation of each of the elongated sections 140 with respect to the first body 130 can be selected to control the direction and magnitude of the forces exerted on surrounding tissue. Further, in certain embodiments, the flexible nature of the elongated sections 140 will allow a high degree of control so that a surgeon or other health care worker can treat wounds having a wide range of sizes and shapes. In addition, in various embodiments, more elongated sections 140 may be used for more irregular or larger wounds, as described further below.

In various embodiments, the first body 130 and elongated sections 140 can include a variety of different structures and/or materials. For example, as shown, the elongated sections 140 can include elongated, flexible wires or cords. These wires or cords can be formed from a variety of suitable materials, including, but not limited to, metals and/or synthetic or naturally occurring polymers. In various embodiments, the elongated sections 140, can be braided, laminated, or of unitary structure. In various embodiments, the specific material and dimensions can be selected based on the amount of force that may be applied to the elongated sections 140 and/or the degree of flexibility suitable for the selected anatomic site. In some embodiments, the first body 130 (as well as the first bodies described below 230, 830, 930) can be produced from a rigid material, such as a rigid plastic or metal, that can withstand tension exerted by elongated extensions 140. In certain embodiments, part or all of the first body 130 can be softer or more pliable.

As noted, the mechanical treatment device 110 can be configured to provide mechanical forces to assist in wound closure, while providing reduced pressure therapy. In various embodiments, a variety of reduced pressure therapy devices can be used. For example, suitable reduced pressure therapy devices include V.A.C.® therapy devices produced by Kinetic Concepts, Inc (San Antonio, Tex.). Such reduced pressure therapy devices can include a vacuum pump, similar to the pump 122 shown in FIG. 1, which can be fluidly connected to the first body 130 of the mechanical treatment device 110. Such devices may also include a flexible sheet 160 to cover the wound site 150 and at least partially seal the wound to allow reduced pressure therapy to be provided at the wound site. In addition, such systems may include a porous material or dressing 180, that is placed at the wound site and facilitates wound closure, healing, tissue regeneration or repair, prevents or treats infection, and/or has other beneficial effects.

In some embodiments, the flexible sheet 160 will include a flexible polymeric material. In various embodiments, any suitable polymeric material can be selected. In various embodiments, the material does not cause significant irritation, immune response, or heightened risk of infection. In various embodiments, the specific material generally should be of sufficient thickness and impermeability to allow reduced pressure therapy at a wound site under the sheet 160. In some embodiments, the connectors 142 may be attached to the flexible sheet 160, while the flexible sheet 160 is attached to underlying skin or other tissue. Accordingly, in various embodiments, the mechanical forces generated by the mechanical treatment device 110 will be at least partially transmitted through the sheet 160, and therefore, the specific material thickness and physical properties will be selected to withstand such physical demands.

In some embodiments, the device 100 will include an adhesive. As used here, and throughout the disclosure, adhesive will be understood to refer to any substance that causes the surfaces of two objects to be attached to one another. In various embodiments, suitable adhesives can include a variety of different cements, glues, resins, or other materials that can facilitate attachment of the flexible sheet 160 to tissue or to other components of the device 100. In some embodiments, the adhesive can include a pressure-sensitive acrylic adhesive. In various embodiments, the adhesives can be applied directly to the structures to be joined, or the adhesives may be applied on tape, or with other supporting substrate materials.

In some embodiments, the adhesive can be applied to a surface of the flexible sheet 160 to attach the sheet to skin or other tissue. In some embodiments, the adhesive will be applied to the surface of the sheet and packaged and/or distributed with the sheet 160. In some embodiments, the adhesive is applied to a surface of the sheet 160 and covered by a nonadhesive material that can be removed to expose the adhesive for use. In certain embodiments, the adhesive can be supplied as a separate component (e.g., in a container or on a tape) that is applied to the sheet 160 to attach the sheet 160 to tissue.

In various embodiments, the porous material 180 can include a variety of suitable materials. For example, a number of different dressing materials are available for use with the above-noted V.A.C.® treatment systems. Such dressings can include, but are not limited to, porous open-cell foam structures, such as open-cell polyurethane. In various embodiments, other materials containing various therapeutic substances can be selected for use with the devices of the present disclosure, and in various embodiments, the specific dressing may be selected based on the particular wound to be treated.

As noted previously, in some embodiments, the connectors 142 attached to the elongated sections 140 can be attached to skin or other tissue, or to the flexible sheet 160 covering a wound site 150 and dressing 180. Certain exemplary configurations for the connectors 142 are described in more detail below. In some embodiments, the connectors 142 can be configured to attach to the flexible sheet, skin, or other tissue without penetrating the sheet, skin, or other tissue. For example, in some embodiments, an adhesive may be placed on an undersurface 516 of the connectors 142 to allow the connectors 142 to be attached to the sheet, skin, or other tissue without penetrating the skin. In some embodiments, the adhesive can include the same adhesive selected to attach the flexible sheet 160 to the patient. In some embodiments, the adhesive can include a pressure-sensitive acrylic adhesive. In some embodiments, the adhesive can be a cyanoacrylate adhesive.

In some embodiments, the connectors 142 can have at least one dimension that is enlarged compared to the elongated sections 140. In some embodiments, the connectors 142 are wider than the elongated sections 140 to which they are attached. In certain embodiments, the connectors 142 have a larger surface area relative to their length to provide a larger surface of attachment.

In various embodiments, the method of attachment of the connectors 142 to the elongated sections 140 can be varied. In certain embodiments, the connectors 142 can be removably attached to the elongated sections 140. In other embodiments, the connectors 142 can be permanently attached to the elongated sections 140. In some embodiments, the connectors 142 can be formed from the same piece of material that forms the elongated sections 140. In certain embodiments, the connectors 142 can be formed from a different piece of material, but can be permanently attached with a weld, chemical bond, or adhesive attachment.

In some embodiments, as shown in FIG. 2, the flexible sheet 160 can be attached over a wound site 150, with at least part of the mechanical treatment device 110 attached to a top surface of the flexible sheet 160. In certain embodiments, the wound is first cleaned and other preparatory procedures are performed. Next, after preparing the wound, a porous material 180 or dressing is selected and cut to an appropriate size before being placed at the wound site 150. Then, after the dressing is positioned in the wound, the flexible sheet 160 is attached over the wound site 150, with the edges of the sheet 160 overlying the wound margins a sufficient distance to allow a seal to be formed to perform reduced pressure therapy.

After the dressing and sheet are positioned over the wound, the first body 130 of the mechanical treatment device 110 is attached to the sheet 160. In some embodiments, the sheet 160 will include a preformed opening or fluid passage to allow the mechanical treatment devices to be attached. In some embodiments, the first body 130 and sheet 160 may be produced and/or distributed as a single unit that is already assembled. In some embodiments, a surgeon can use a sheet having no opening or preformed attachment for the first body 130, but may produce the opening and attach the first body 130 using an adhesive, such as that used to attach the connectors 142 and/or sheet 160. In some embodiments, the sheet 160 can include a tubular member attached to the sheet 160 through a preformed passage, and the first body 130 can be configured to attach to this tubular member to provide fluid communication with an underlying wound.

After the first body 130 is attached to the sheet 160, the connectors 142 can be positioned on the sheet 160. As noted previously, the connectors 142 may be attached to the sheet 160 using an adhesive to attach undersurfaces 516 of the connectors 142 to the sheet. Accordingly, with the sheet 160 being adhesively attached to the patient's skin or other tissue, and the mechanical treatment device 110 being attached to the sheet 160, forces generated in the elongated sections 140 are transmitted to the patient's tissue, thereby mechanically coupling the device 110 to the area surrounding the wound and drawing the wound margins closer together.

Figure 3:
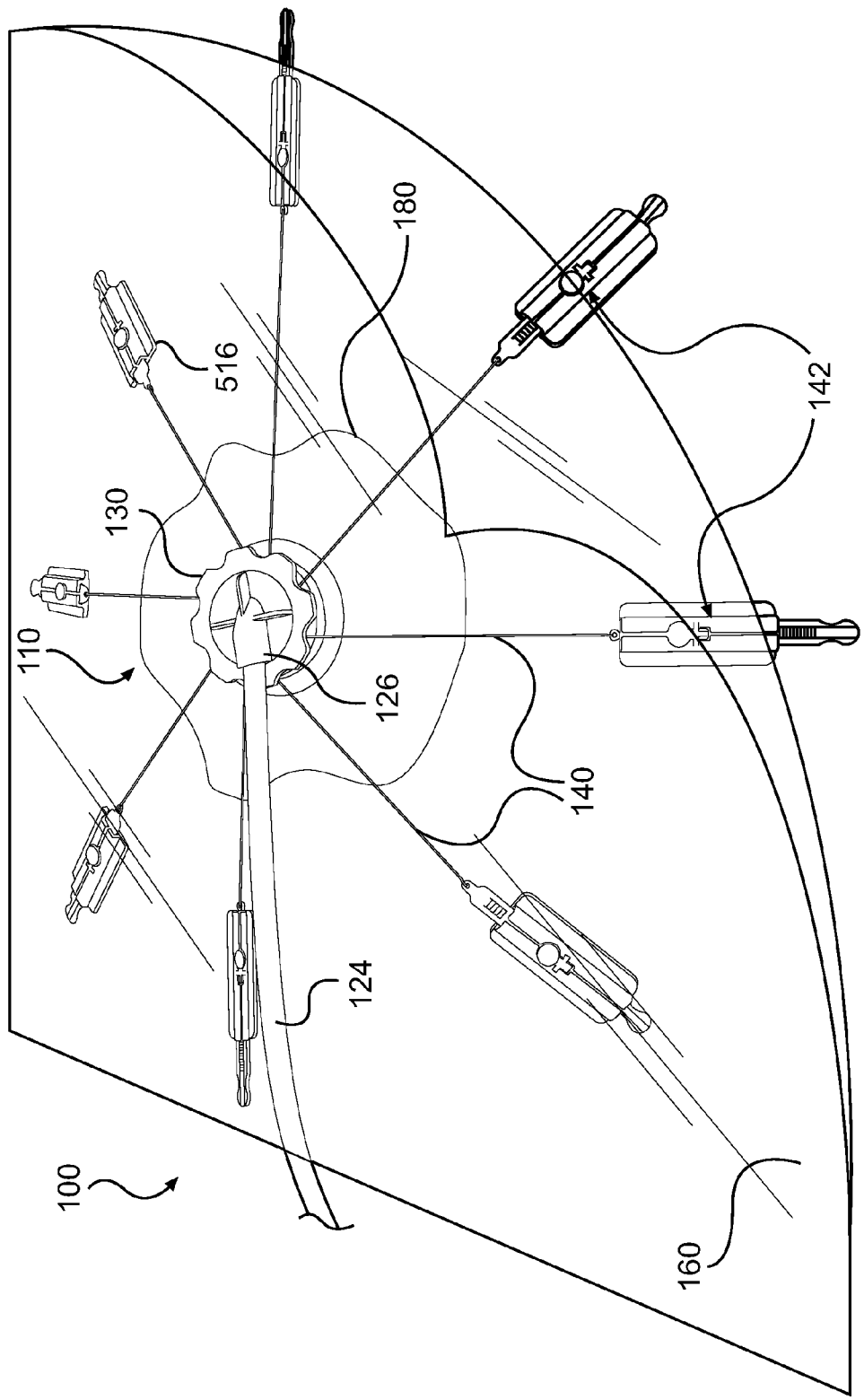
FIG. 3 illustrates another embodiment of the wound treatment device of FIG. 1.

In certain embodiments, the mechanical wound treatment device 110 can be attached directly to the skin or other tissue around a wound site to mechanically couple the device 110 to the tissue around the wound and draw the wound margins closer together. For example, FIG. 3 illustrates certain embodiments of the wound treatment device 100 of FIG. 1. As shown, the device 100 again includes a mechanical wound treatment device 110 having a number of elongated sections 140 extending in different directions from a first body 130. The first body 130 further includes a connector 126 configured to engage a reduced pressure therapy device 120, as described previously. However, in such embodiments, the mechanical treatment device 110 is attached to tissue surrounding the wound site before the flexible sheet 160 is applied to seal the wound. Therefore, the undersurfaces 516 of the connectors 142 are adhesively attached directly to skin or other tissue. Further, the fluid passage or tubing 124 of the reduced pressure therapy device 120 can pass under the sheet 160. Alternatively, in various embodiments, the fluid passage 124 and/or the first body 130 of the mechanical treatment device 110 can protrude through an opening (not shown) formed in the sheet 160, thereby allowing access to these elements when the sheet is applied.

As shown in FIG. 3, in some embodiments, the sheet 160 may be sized such that when placed over the mechanical wound treatment device 110, the sheet will cover the first body 130, the elongated sections 140, and each of the connectors 142. In some embodiments, the sheet 160 covers the first body 130 and wound, while the connectors 142 are not covered by the sheet 160, but remain attached to tissue. In some embodiments, the sheet 160 will be sized so that one or more connectors 142 are not covered to allow easy manipulation of the connectors 142.

Figure 4:
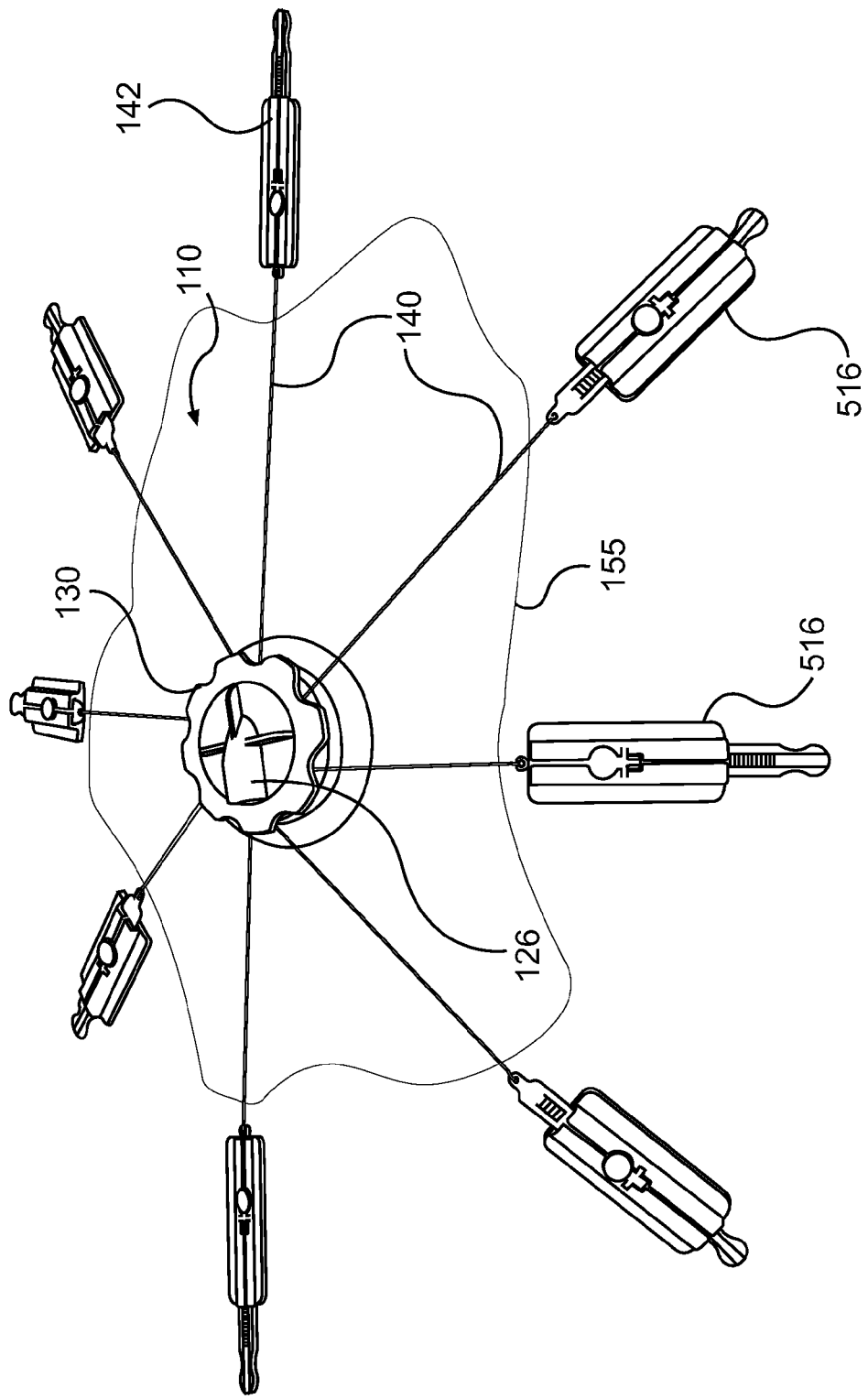
FIG. 4 illustrates certain exemplary embodiments of the wound treatment device of FIG. 1, which includes additional elongated sections.

As noted previously, in various embodiments, the wound treatment devices of the present disclosure can be used to treat wounds having a variety of different types, shapes, sizes, and locations. For example, FIG. 4 illustrates certain embodiments of the wound treatment device 100 of FIG. 1, being used to treat a more irregularly shaped wound 155. Various elements in FIG. 1 that are not shown in FIG. 4 can be used with the embodiments in FIG. 4.

As shown in FIG. 4, the mechanical treatment device 110 includes eight elongated sections 140 extending in various directions. Further, the positions of the connectors 142 with respect to the margins of the wound 155 have been adjusted to conform to the irregularities of the wound 155. Therefore, in various embodiments, the mechanical treatment devices provide flexibility in treating a variety of different shapes and sizes of wounds by allowing control of the number, length, and position of elongated sections that produce tensile forces to assist in tissue stretching and/or wound closure.

In addition to adjusting positions of the connectors 142 by moving the elongated sections 140, the length and position of the elongated sections 140 and/or connectors 142 can be controlled in a number of other ways to allow the connectors 142 to be appropriately positioned around a wound. For example, in some embodiments, the length of the connectors 142 can be adjusted. In other embodiments, the position at which the connectors 142 attach to the elongated sections 140 can be adjusted to control the distance from the first body 130 to the connectors 142.

Figure 5A:
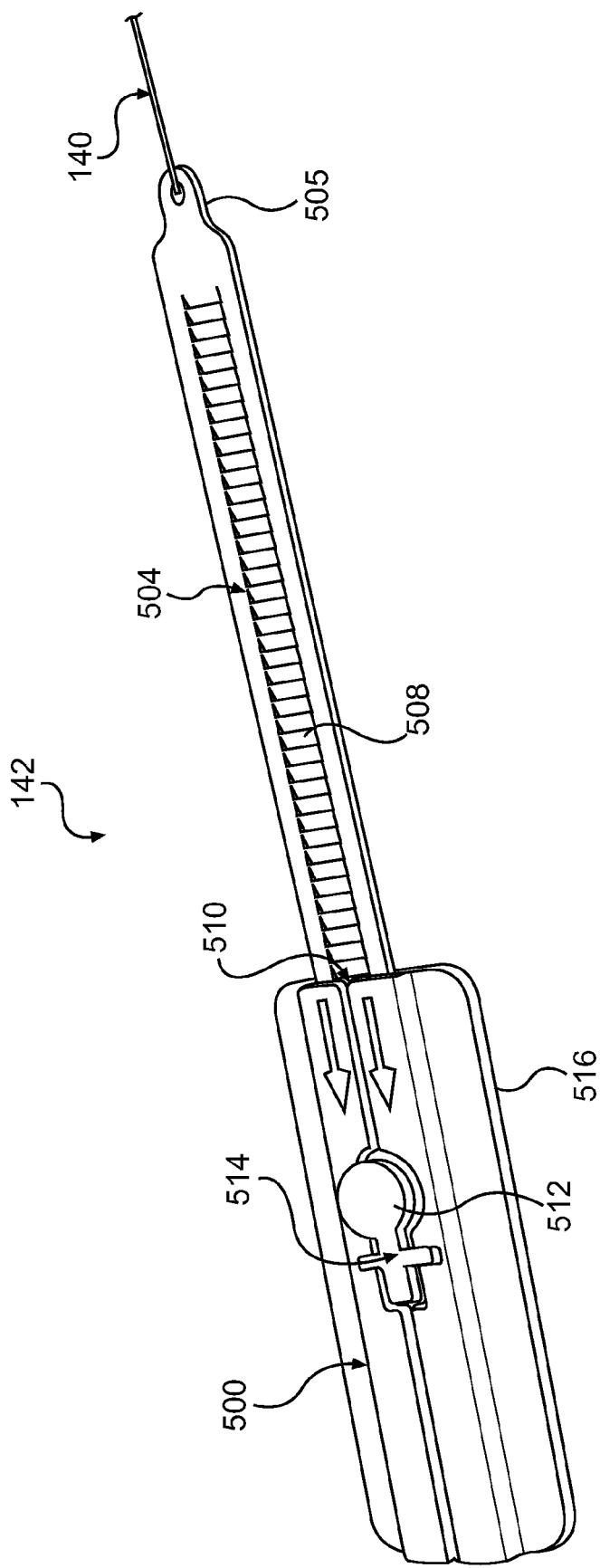
FIG. 5A illustrates an adjustable connector attached to an elongated section of a mechanical wound treatment device, according to certain exemplary embodiments.
Figure 5B:
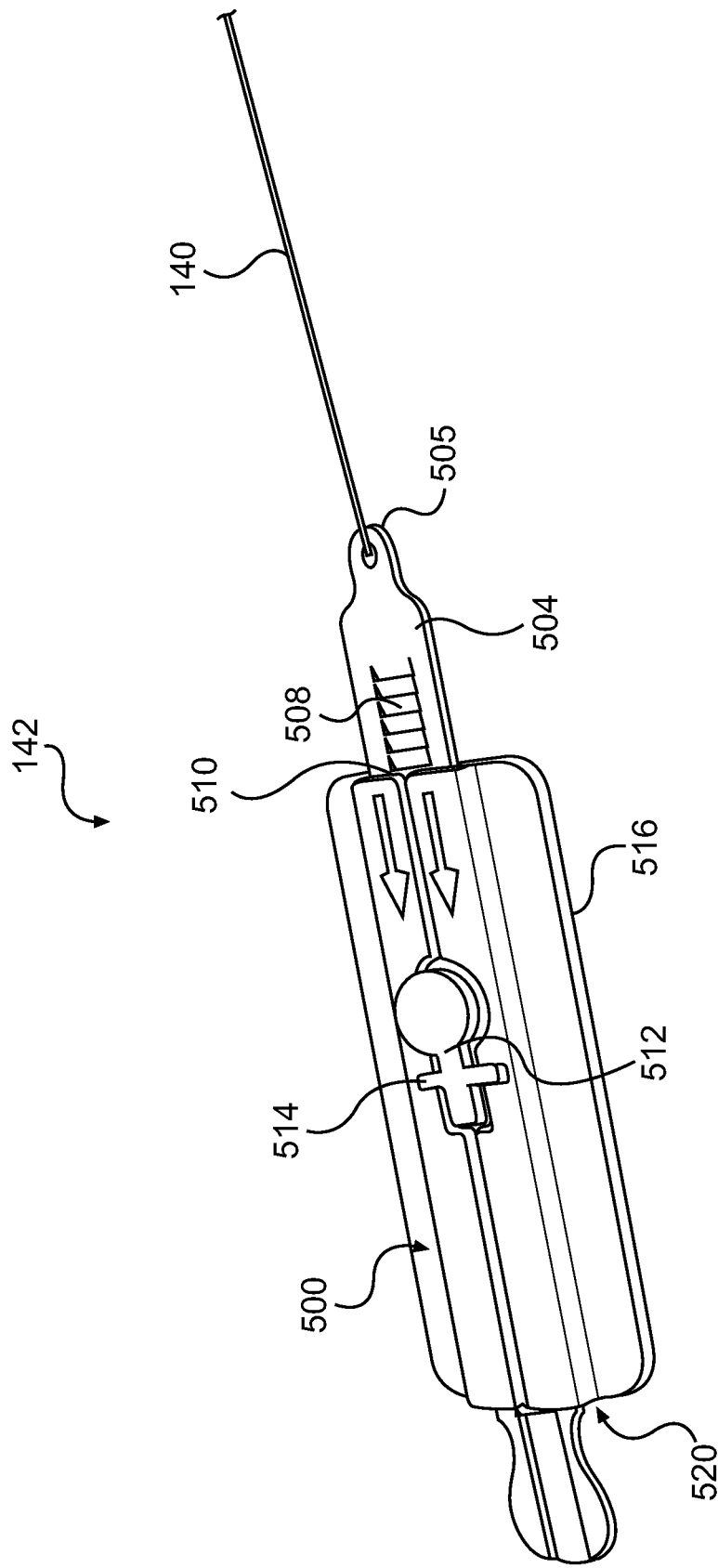
FIG. 5B illustrates the adjustable connector of FIG. 5A in a shortened position.

In some embodiments, the connectors 142 can include an adjustable length, thereby allowing control of the distance from the first body 130 to the position of attachment of the connector 142 to the patient's tissue or the sheet 160. FIGS. 5A-5B illustrate certain embodiments of an adjustable connector 142. FIG. 5A illustrates the adjustable connector in a more elongated configuration, and FIG. 5B illustrates the adjustable connector of FIG. 5A in a shortened configuration.

As shown, the connector 142 includes a tab portion 504 having a series of notches or ridges 508 along its length. Further, a proximal end 505 of the tab portion 504 is attached to the elongated section 140. The connector 142 further includes a tab receiving portion 500 having an undersurface 516 that can be adhesively attached to a patient's tissue or a flexible sheet 160, as described above. As shown, the tab receiving portion 500 includes an opening and passage 510 configured to receive the tab portion 504. Further, as the tab portion 504 is advanced into the passage 510, the ridges or notches 508 will engage an inwardly protruding portion 514 of a locking mechanism 512, thereby securing the tab portion 504 within the tab receiving portion 500. In some embodiments, the locking mechanism 512 prevents sliding movement of the tab portion 504 within the tab receiving portion 500 in one direction, while allowing sliding movement in the opposite direction. In some embodiments, the locking mechanism 512 allows the tab portion 504 to slide into the tab receiving portion 500, thereby shortening the distance from the tab receiving portion 500 to the end of the elongated section 140 attached to the tab portion 504, and prevents movement of the tab portion 504 out of the tab receiving portion 500, thereby preventing an increase in the distance from the tab receiving portion 500 and the end of the elongated section 140 attached to the tab portion 504.

As shown, the tab portion 504 can be advanced a desired distance within the tab receiving portion 500, thereby adjusting the distance between the tab receiving portion 500 and the end of the elongated section 140 attached to the tab portion 504, and controlling the overall length of the connector 142. For example, as shown in FIG. 5B, the tab portion 504 can be advanced nearly completely to shorten the distance between the tab receiving portion 500 and the end of the elongated section 140 attached to the tab portion 504. Alternatively, by advancing the tab portion 504 a shorter distance into the tab receiving portion 500, the distance between the tab receiving portion 500 and the end of the elongated section 140 attached to the tab portion 504 can be increased.

The length of the connectors 142 can be adjusted either before the connectors 142 are attached to a patient's tissue or a sheet 160 or after the connectors 142 are attached to the patient's tissue or sheet 160. In some embodiments, the tab receiving portion 500 is attached to tissue or a sheet 160, and then the tab portion 504 is inserted or adjusted within the tab receiving portion 500 to produce increased tension in the elongated section 140 attached to the tab portion 504. In some embodiments, the tab portion 504 is adjusted to a selected position within the tab receiving portion 500, and then the tab receiving portion 500 is attached to tissue or the sheet 160.

Figure 6B:
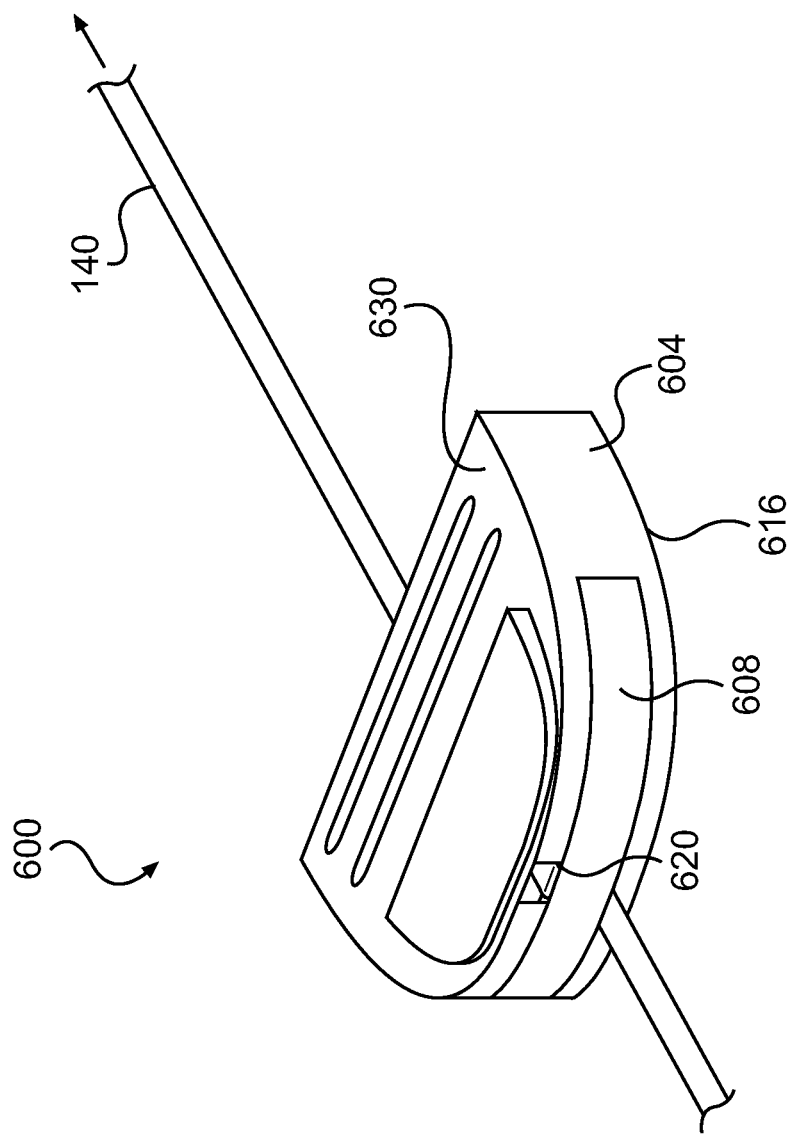
FIG. 6B illustrates the adjustable connector of FIG. 6A in a closed and fixed position on the elongated section.

In various embodiments, the distance of the connectors from the first body 130 can be controlled by adjusting the position of the connectors along the elongated section 140. FIGS. 6A-6B illustrate an adjustable connector 600 and an elongated section 140 of a wound treatment device, according to certain exemplary embodiments. In these embodiments, the connector 600 is adjustably positioned along the length of the elongated section 140. As shown, the connector 600 includes a connector main body 604 and a locking body 608. In some embodiments, the locking body 608 includes an opening 612 for receiving the elongated section 140, while the connector main body 604 includes a groove 620 for receiving the elongated section 140. In some embodiments, a cover 630 is attached to the top of the main body 604 to cover the groove 620.

As shown in FIG. 6A, the connector 600 can be adjusted along the length of the elongated section 140. Then, in order to lock the connector 600 in place, the locking body 608, with the elongated section 140 passing through the groove 620 and opening 612, is pushed into a slot 610 of the connector main body 610, thereby applying pressure to the elongated section 140 to crimp the elongated section 140 and secure the connector 600 in place along the elongated section 140.

In various embodiments, the locking body 608 and slot 610 can be sized such that a press fit connection is formed upon inserting the locking body 608 into the slot 610, along with the elongated section 140. In some embodiments, the pressure formed by this connection will be sufficient to hold the connector 600 in place on the elongated section 140. In some embodiments, an adhesive or other connection mechanism may be used to secure the locking body 608 within the slot 610.

In a manner similar to the connector 142, the connector 600 can be attached to a patient's tissue or a sheet 160 using an adhesive. In certain embodiments, after the connector 600 is positioned on the elongated section 140 and fixed in place, as described above, an adhesive can be applied to, or exposed on (e.g., on a surface of two-way tape), a bottom surface 616 of the connector 600 or a tissue or sheet surface to which the connector 600 is to be attached. Further, as described above, in certain embodiments, after each of the connectors 600 have been attached to the patient's tissue or the sheet 160, the mechanical treatment device can be tightened to produce a desired degree of tension in the tissue surrounding the wound.

In various embodiments, the first body 130 can include a number of mechanisms to facilitate tightening of the elongated sections 140 to produce the desired amount of tension in the surrounding tissue. In some embodiments, the first body 130 can include a rotatable portion for shortening the elongated sections 140, thereby increasing tension and/or stretching surrounding tissue.

Figure 7A:
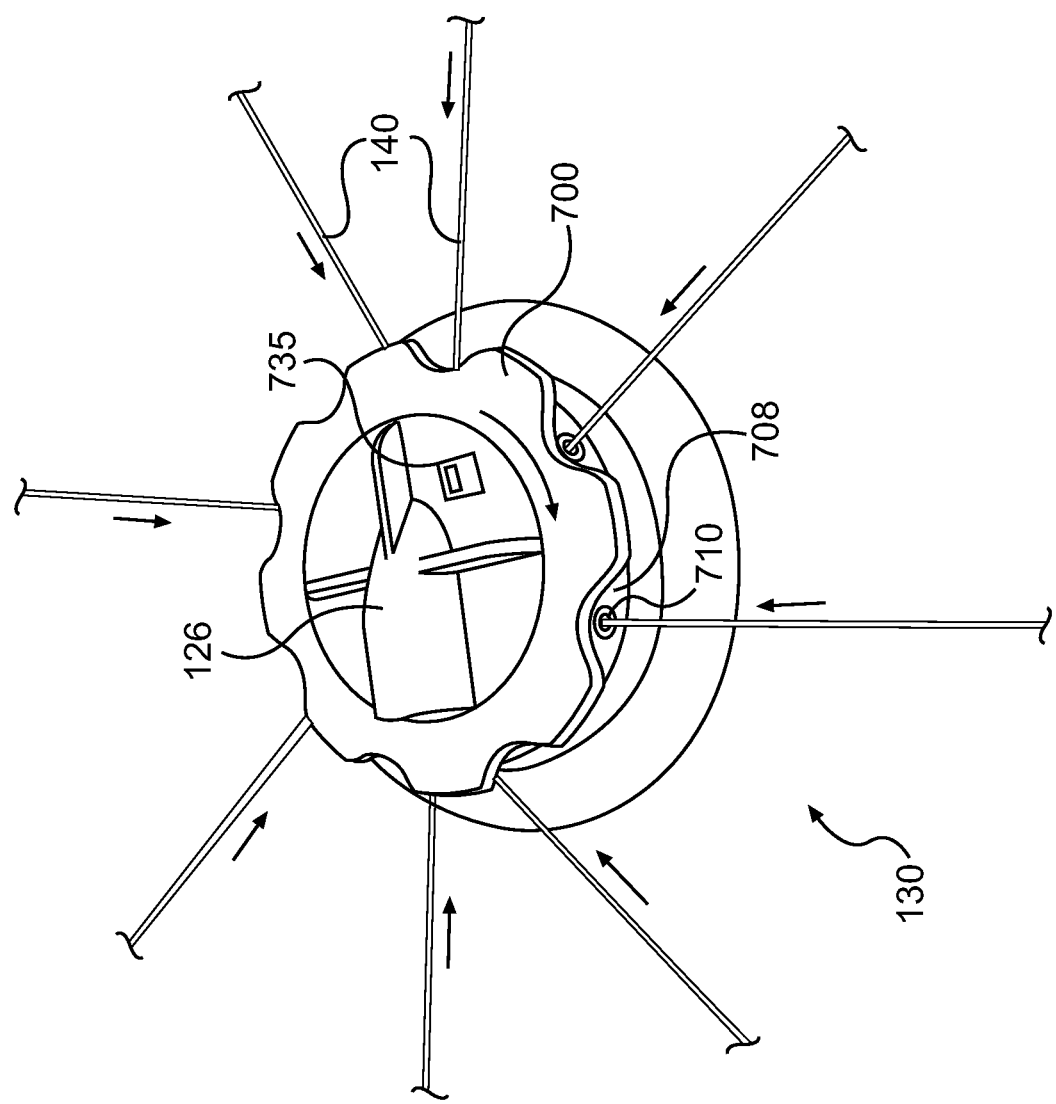
FIG. 7A illustrates an enlarged view of a first body of a wound treatment device, including a tightening or tension-producing mechanism, according to certain exemplary embodiments.
Figure 7B:
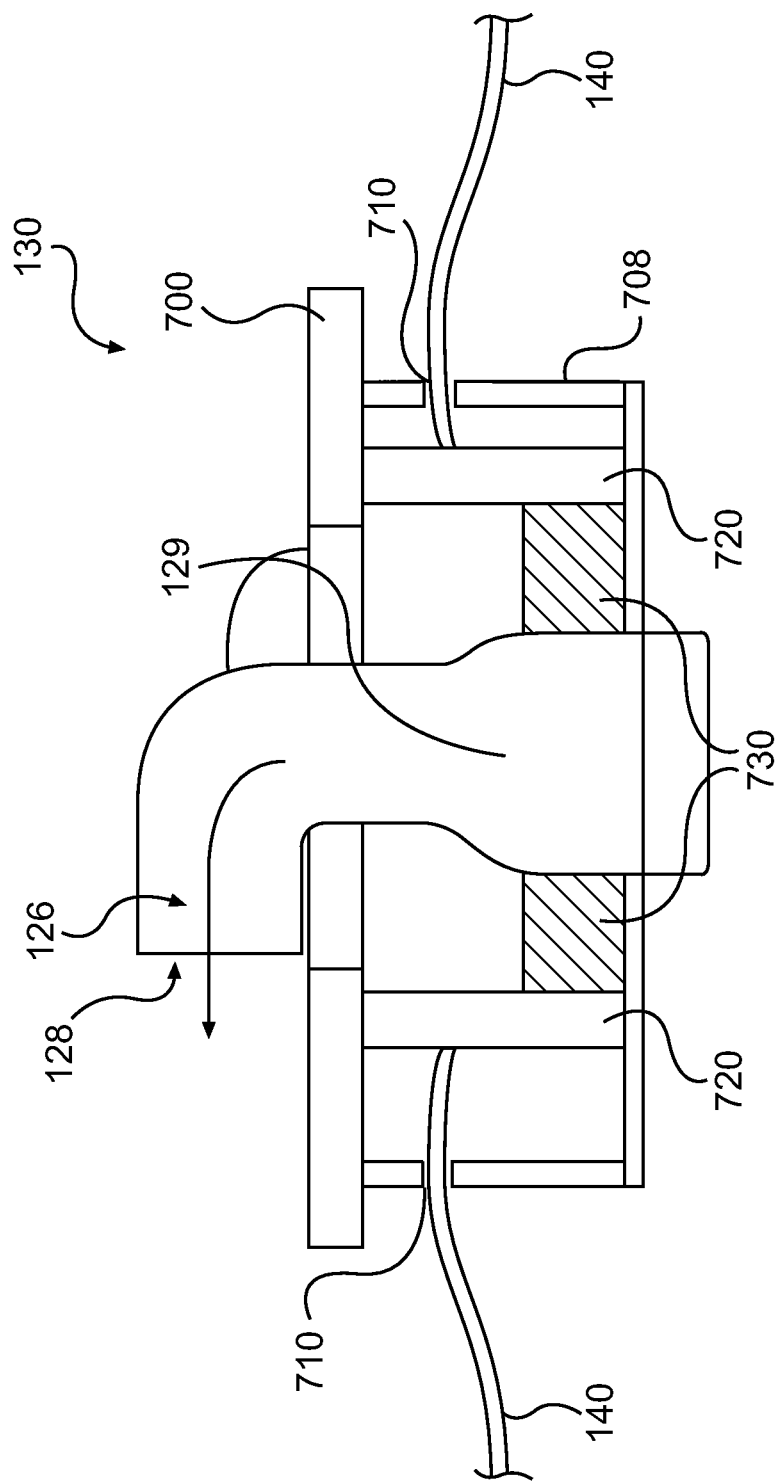
FIG. 7B illustrates a partial cut-away view of the device of FIG. 7A, showing internal components of the device.

FIG. 7A illustrates an enlarged view of the first body 130, according to certain exemplary embodiments, and FIG. 7B illustrates a partial cutaway view of the first body 130 of FIG. 7A. As shown, the elongated sections 140 extend from the first body 130 in various directions. Further, as noted previously, in various embodiments, the number and position of each elongated section 140 can vary or be adjusted based on the particular wound to be treated.

As shown in FIGS. 7A and 7B, the first body 130 includes a rotatable portion 700. In various embodiments, the rotatable portion 700 is operably engaged with an internal wall 720 (shown in FIG. 7B) to which the elongated sections 140 are attached. In some embodiments, the internal wall 720 has a substantially cylindrical shape, and the elongated sections 140 are attached to the surface of the internal wall 720. Therefore, as the rotatable portion 700 is rotated, the internal wall 720 rotates. As the internal wall 720 rotates, the elongated sections 140, which are attached to the internal wall 720, are at least partially wrapped around the internal wall 720. In some embodiments, wrapping of the elongated sections 140 around the internal wall 720 causes the distance that the elongated sections 140 extend from the first body 130 to be decreased to produce a desired tension in tissue attached to the connectors 142 or the sheet 160, as described above. In some embodiments, rotation of the rotatable portion 700 in one direction decreases the distance that the elongated sections 140 extend from the first body 130. In certain embodiments, rotation of the rotatable portion 700 in a second direction opposite the first direction increases the distance the elongated sections 140 extend from the first body 130.

In various embodiments, it will be desirable to immobilize the rotatable portion 700, and therefore fix the length that the elongated sections 140 extend from the first body 130 after tightening to a desired degree. Therefore, in some embodiments, the first body 130 can further include a locking mechanism 730 operably engaged with the inner wall 720 and/or rotatable portion 700. In some embodiments, the locking mechanism 730 can be configured to allow rotation or tightening in one direction but not the other, thereby allowing tightening by twisting the rotatable portion 700, and preventing loosening by preventing counter rotation. In some embodiments, the locking mechanism 730 can include a ratchet mechanism or a ratchet and pawl, as are known in the art. Further, in certain embodiments, the ratchet mechanism can be reversible to allow tightening and loosening when desired. In various embodiments, the first body 130 can include a release mechanism 735. In some embodiments, the release mechanism 735 can include a button or switch that can control operation of the locking mechanism 730 to engage, disengage, or reverse direction of the locking mechanism 730. In some embodiments, the release mechanism 735 can reverse the direction of operation of the locking mechanism 730 to allow rotation in a first direction but not a second direction, or to allow rotation in the second direction but not the first direction. In some embodiments, the release mechanism 735 can disengage the locking mechanism 730 to allow rotation in either direction.

As shown, in certain embodiments of FIGS. 7A and 7B, the first body 130 can further include an outer wall 708 having openings 710 through which the elongated sections 140 can pass before attaching to the inner wall 720. In some embodiments, these openings can have a fixed position about the periphery of the first body 130. In some embodiments, the openings does not move as the rotatable portion 700 is moved, thereby controlling the direction along which the elongated sections 140 exert force on surrounding tissue, even as the elongated sections 140 are tightened.

In addition, as noted previously, in some embodiments, the wound treatment devices 100 can allow mechanical treatment in conjunction with reduced pressure therapy. Accordingly, as shown in FIG. 7B, the first body 130 further includes a connector 126 configured to engage the fluid passage 124 of a reduced therapy system pump 122. As shown, the connector 126 includes an opening 128 that can be fluidly connected with the fluid passage 124. The opening 128 is in fluid communication with a fluid passage 129 that passes through the first body 130 and is in fluid communication with a wound and dressing to provide reduced pressure therapy.

Figure 8A:
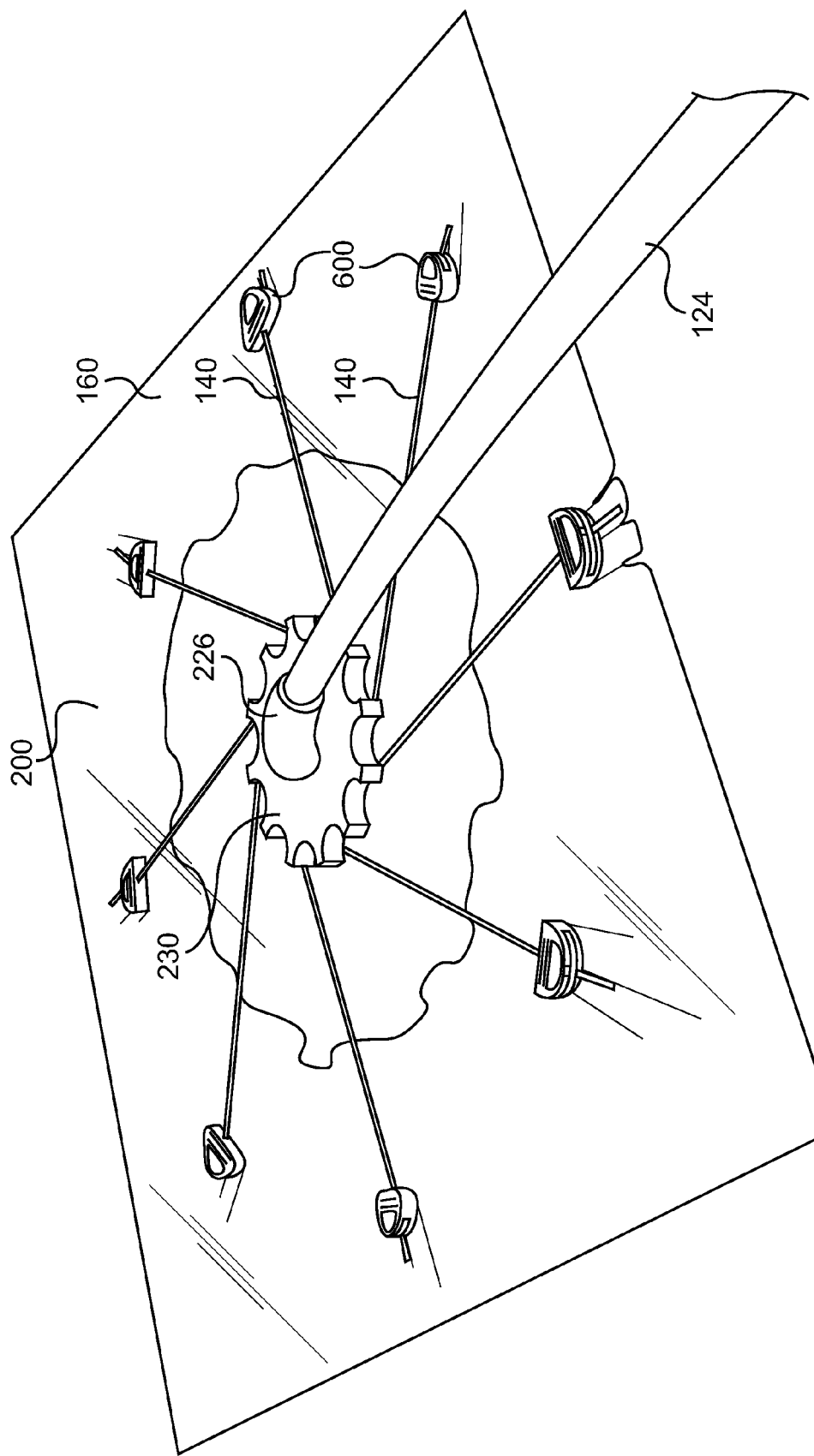
FIG. 8A illustrates a wound treatment device according to certain exemplary embodiments.

FIG. 8A illustrates a wound treatment device 200, according to certain exemplary embodiments. As shown, the device 200 includes a mechanical treatment device 210, also including a first body 230, similar to first body 130. Further, the device 210 includes a number of elongated sections 140 extending at various directions and being attached to a sheet 160 overlying and sealing a wound to be treated. As shown, the elongated sections 140 are attached to the sheet using connectors 600, as described with respect to FIGS. 6A and 6B. In various embodiments, any of the connectors described herein may be used.

Figure 8B:
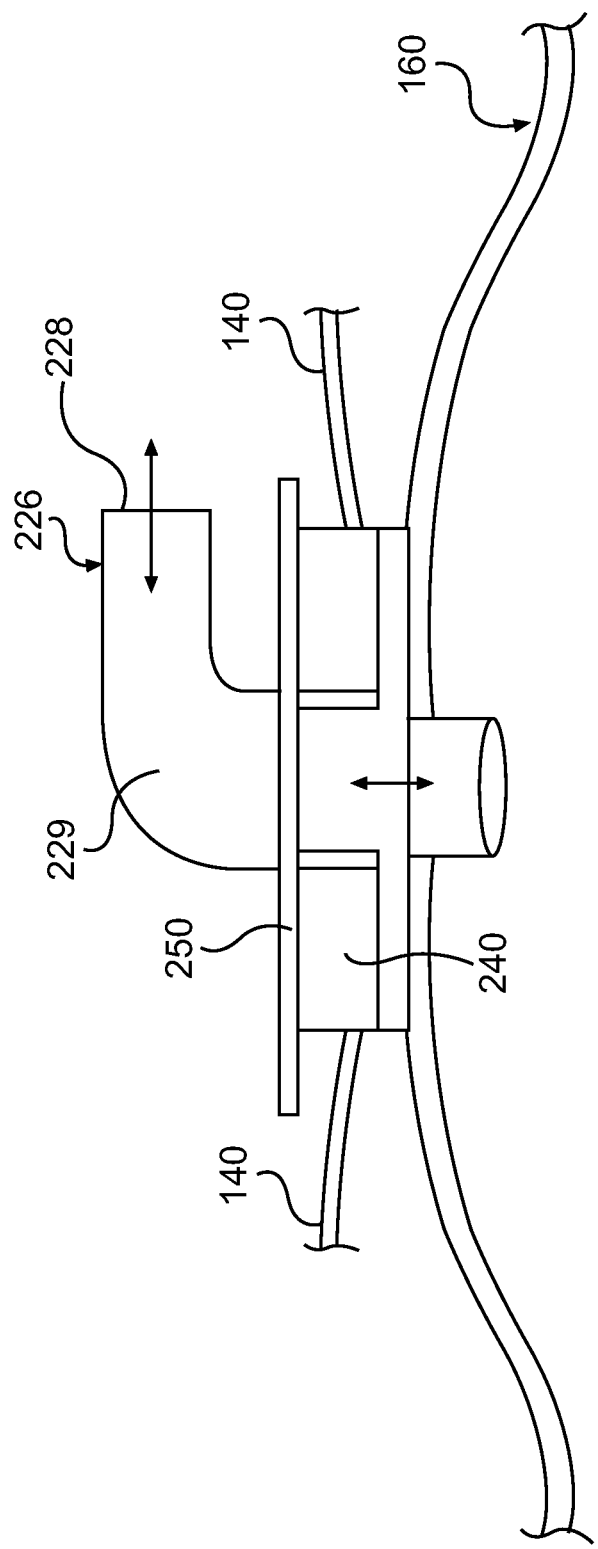
FIG. 8B illustrates a partial cut-away view of the device of FIG. 8A, showing internal components of the device.

FIG. 8B illustrates a partial cut-away view of the device of FIG. 8A, showing internal components of the device. As shown, the first body 230 includes a rotatable portion 250 attached to a spool or tightening mechanism 240. Each of the elongated sections 140 are attached to the spool or tightening mechanism, so that as the rotatable portion 250 is rotated, the tightening mechanism is engaged to increase tension in the elongated sections 140, thereby pulling wound margins mechanically coupled to the connectors 600 closer together.

Further, as described above with respect to the first body 130, in certain embodiments, the device 200 can include an internal locking mechanism, such as a ratchet system that allows rotation in one direction, while preventing counter rotation. In some embodiments, the spool or tightening mechanism 240 can include a series of gears to provide a mechanical advantage, allowing increased tension to be produced in the elongated sections 140 without excessive effort directed at turning the rotatable portion 250.

In certain embodiments, as noted above, the first body 230 can be configured to facilitate mechanical wound closure, while allowing reduced pressure therapy. Accordingly, in certain embodiments, the first body 230 can include a fluid connector 226 that can be fluidly coupled with a pump 122 via a fluid passage 124. The fluid connector 226 can include an opening 228 and can communicate with a fluid passage 229 traversing the first body 230 to provide fluid communication with a wound.

Figure 9:
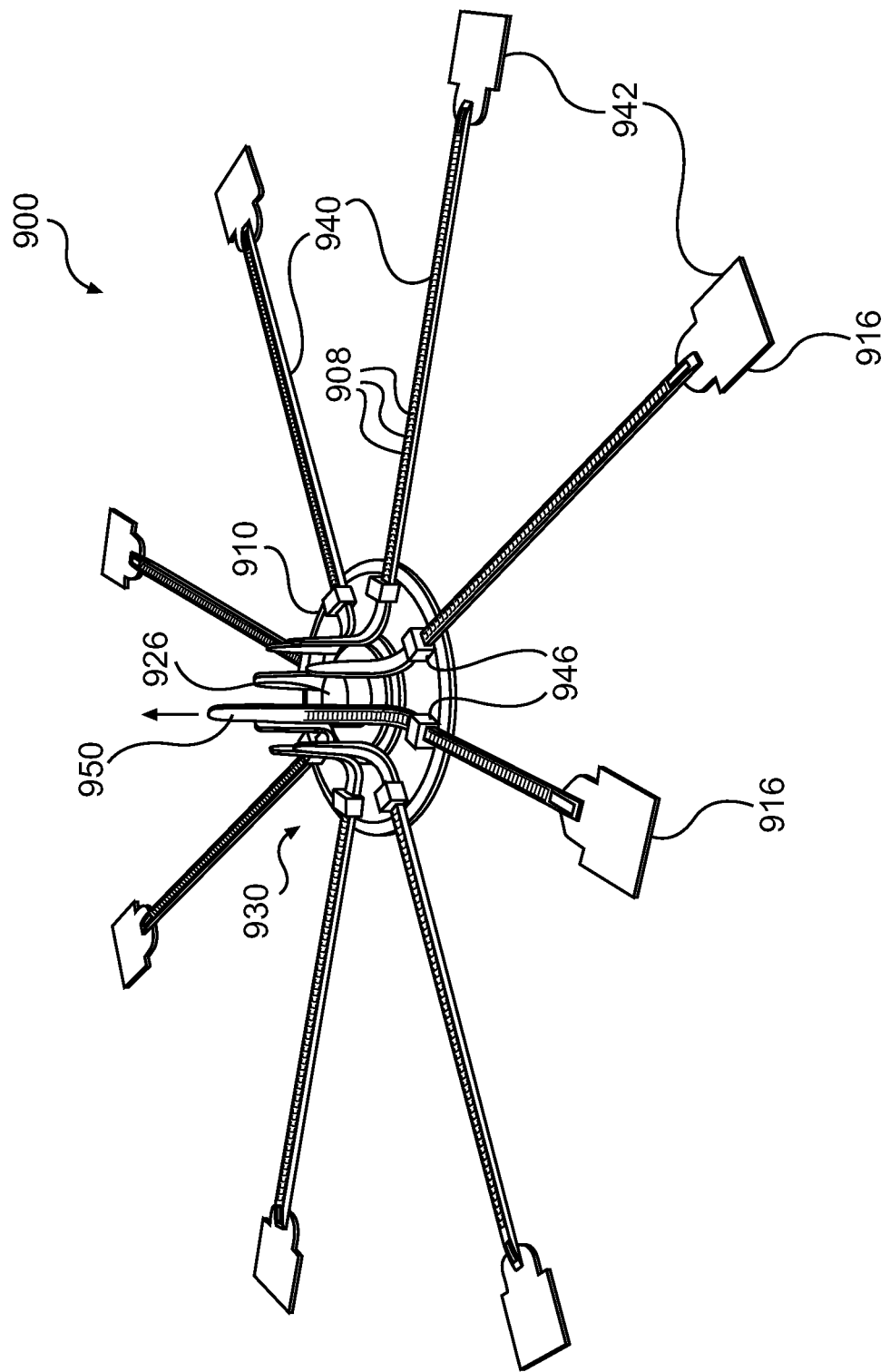
FIG. 9 illustrates a wound treatment device according to certain exemplary embodiments.

FIG. 9 illustrates certain exemplary embodiments of a wound treatment device 900. As with certain previously described devices, the device 900 includes a first body 930 having two or more elongated sections 940 extending from the first body 930 and including connectors 942 configured to be adhesively attached to a patient's tissue or a flexible sheet 160 (not shown) using at surfaces 916. Further, the device 900 includes a connector 926 configured to engage a reduced pressure therapy device 120, as described previously.

In these embodiments, however, each of the elongated sections 940 are adjustably connected to the first body 930 at elongated section receiving portions 946. Here, proximal end portions 950 of the elongated sections 940 are passed through the elongated section receiving portions 946, which, in some embodiments, include a female connector opening configured to receive a corresponding proximal end portion 950 forming a male connector portion of the elongated sections 940. Further, the end portions 950 can be pulled further through the attachment regions 946 to shorten the length of each elongated section 940 extending from the first body 930 to produce the desired tension in each elongated section 940. In some embodiments, after adjusting the length of the elongated sections 940, the end portion 950 may be removed or cut off to reduce the device size and allow placement of an overlying sheet, if desired. In some embodiments, the elongated sections 940 can include small ridges or notches 908 to allow the elongated sections 940 to be pulled through the elongated section receiving portions 946, and provide a locking mechanism that prevents the elongated sections 940 from being pulled back out of the openings after tightening. In various embodiments, the specific locking mechanism can be selected based on the desired degree of tension to be produced, but one suitable mechanism is similar to that used in devices conventionally described as plastic handcuffs or ties.

Figure 10:
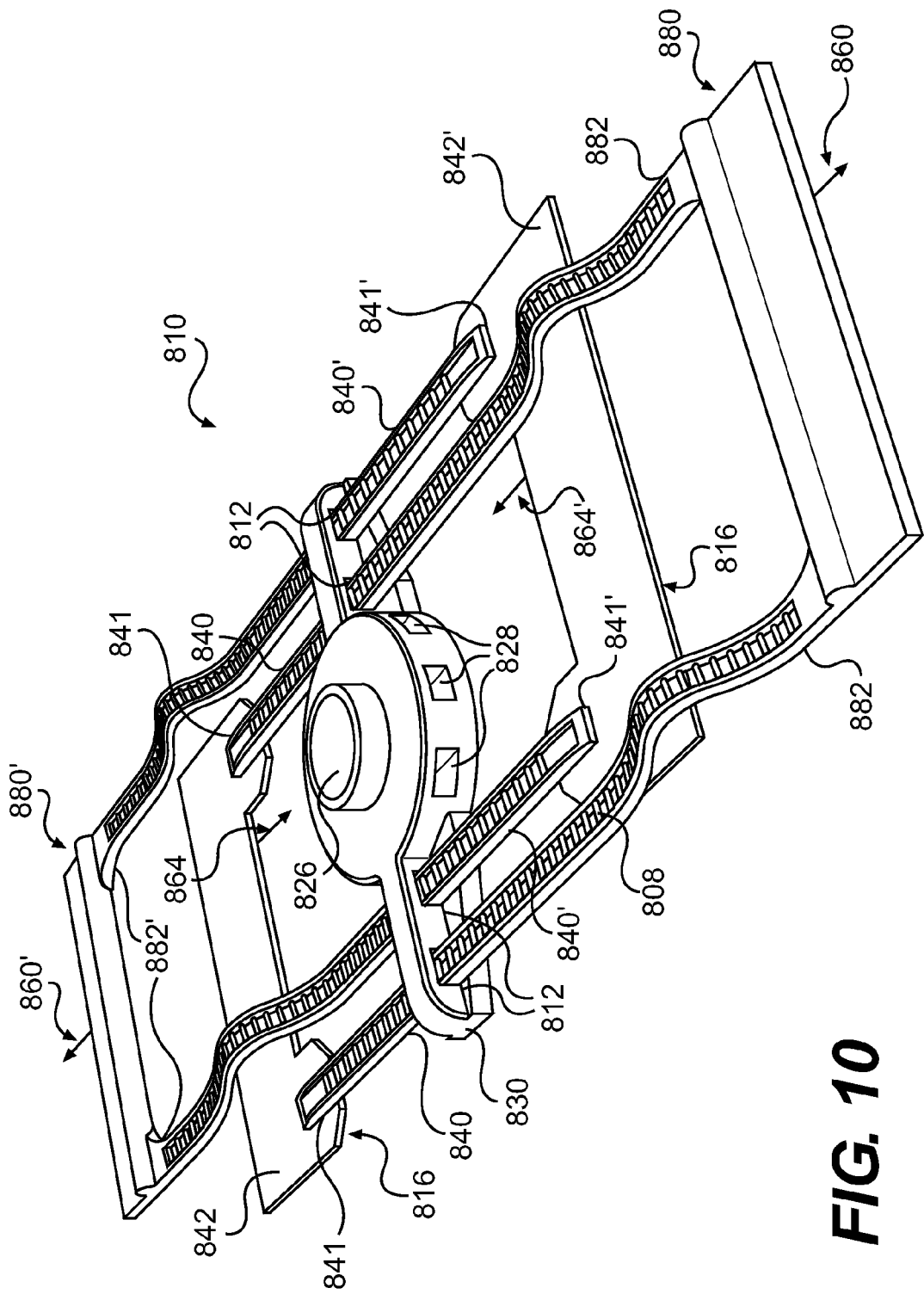
FIG. 10 illustrates a wound treatment device according to certain exemplary embodiments.
Figure 11:
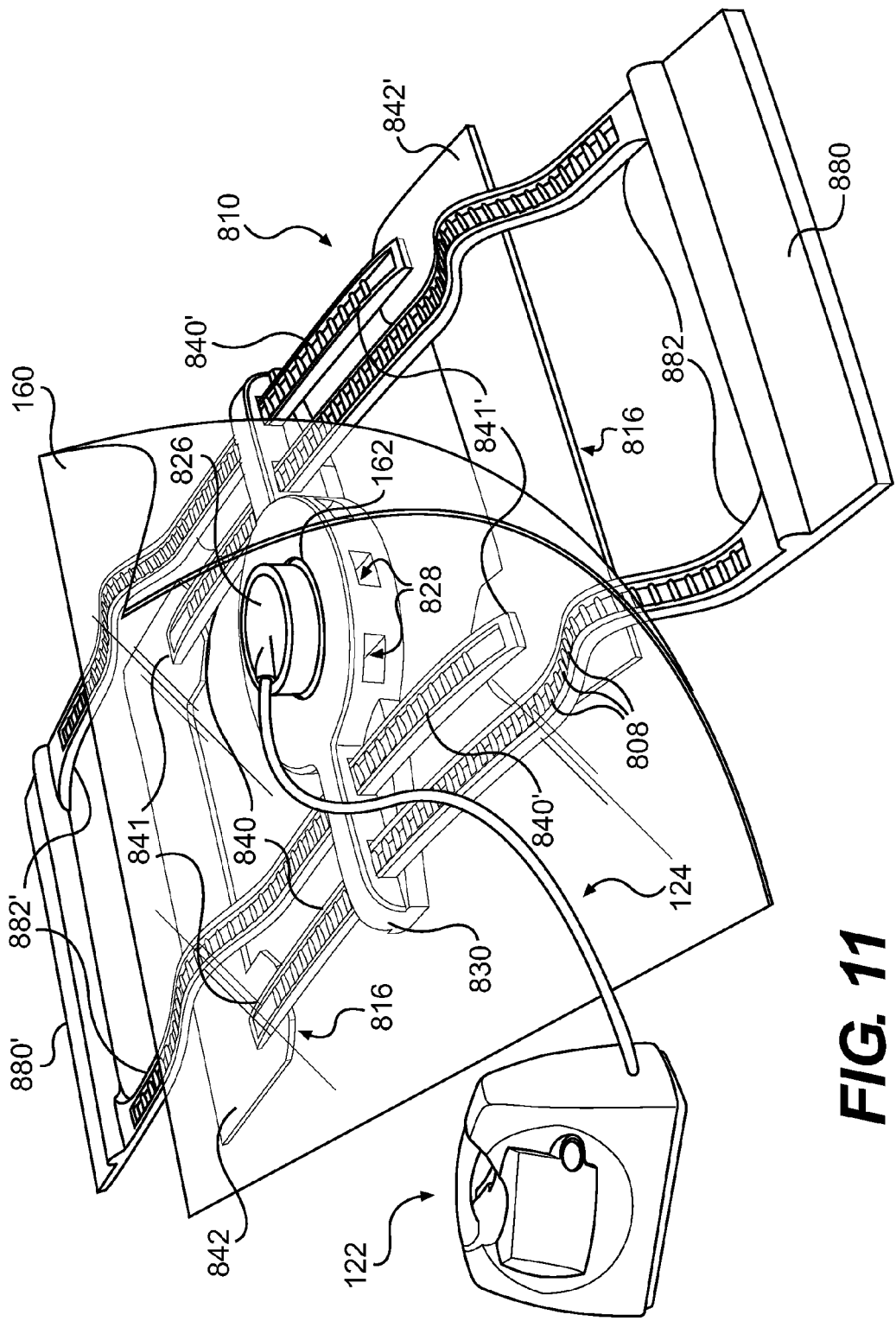
FIG. 11 illustrates the wound treatment device of FIG. 10, including reduced pressure therapy treatment components.

As noted above, in various embodiments the wound treatment devices can be used for wounds having linear or irregular shapes. FIG. 10 illustrates a mechanical wound treatment device 810 for use with substantially linear wounds, according to certain embodiments, and FIG. 11 illustrates the wound treatment device of FIG. 10, along with a reduced pressure treatment device. As shown, the device 810 includes a first body 830. Two pairs of elongated sections 840, 840' extend from the first body 830. In certain embodiments, each of the elongated sections 840, 840' includes a pair of substantially parallel elongated arms. In addition, a connector 842, 842' extends between first end regions 841, 841' of each pair of elongated arms of the elongated sections 840, 840', forming a flattened or enlarged region that can be attached to a patient's skin or other tissue, or to a sheet 160 overlying a wound. Each of the arms of the elongated sections 840, 840' can pass through openings 812 in the first body 830 and will extend to second ends 882, 882' of the elongated arms on opposite sides of the first body 830 from the connectors 842, 842'. In certain embodiments, handle regions 880, 880' extend between the second end regions 882, 882' of each of the pair of elongated arms.

As noted, the connectors 842, 842' may be attached to tissue or a sheet around a wound site. In some embodiments, the connectors 842, 842' can be attached using an adhesive, as described previously, thereby allowing force to be exerted on tissues surrounding the wound without penetrating skin or other tissue.

In some embodiments, after the connectors 842, 842' are attached to tissue surrounding a wound, or to a sheet 160 overlying a wound, the connectors 842, 842' can be pulled together to exert forces that assist in closing the wound or approximating wound edges. This force can be produced by pulling the handle regions 880, 880' apart in the direction 860, 860' indicated in FIG. 10, thereby drawing the connectors 842, 842' together in the direction 864, 864' indicated in FIG. 10.

In certain embodiments, in order to keep the connectors 842, 842' in place, thereby allowing continued force to be applied to wound margins, the first body 830 and elongated sections 840, 840' can include a locking mechanism. For example, in certain embodiments, the elongated sections 840, 840' can include ridges or notches 808 along at least one of their surfaces, and the first body 830 can include an inner mechanism that prevents movement of elongated sections 842, 842' in one or both directions.

In some embodiments, the first body 830 can include additional openings 828 to receive elongated sections. In some embodiments, the additional openings 828 can be positioned to allow the elongated sections 840, 840' to be positioned at different positions along the length of the first body 830. In some embodiments, the openings 812 and additional openings 828 can be configured to receive elongated sections having other configurations. For example, in certain embodiments, the elongated sections 940 (as shown in FIG. 9) can be used with the first body 830 shown in FIG. 10. In some embodiments, two or more of the elongated sections 940 will attached to the first body 830 so that elongated sections 940 extend in opposite directions from the first body 830. In some embodiments, multiple elongated sections 940 will extend from the first body 830 to provide mechanical forces along the length of a linear wound.

As noted previously, the mechanical treatment devices of the present disclosure can be designed to facilitate mechanical treatment to assist in wound closure, while allowing reduced pressure therapy. Accordingly, the device 810 can include a fluid connector 826 configured to connect to a fluid passage 124 of a reduced pressure therapy device, as shown in FIG. 11. As discussed above, in certain embodiments, the fluid connector 826 can be fluidly connected with fluid passages that transverse the first body 830, providing fluid communication with a wound site underlying the device 810. In some embodiments, the fluid connector 826 can be connected to a fluid passage passing downward to a bottom surface of the first body 830. In some embodiments, the fluid passages may be positioned along the side or at other positions along the first body 830. For example, in some embodiments, one or more of the openings 828 can form fluid passages in fluid communication with the fluid connector 826.

In certain embodiments, after the device 800 has been attached to a wound and the reduced pressure therapy pump 122 has been engaged, a sheet 160 can be placed over the apparatus 800 to seal the wound and allow both mechanical treatment and reduced pressure therapy. In some embodiments, the sheet can include an opening 162 to allow the fluid connector 826 to pass through the sheet. In addition, like certain devices described above, in certain embodiments, the sheet 160 may be positioned under the mechanical treatment device 800, and the device can be adhesively attached to the sheet 160 to transmit mechanical forces to tissues located beneath the sheet 160.

In certain embodiments, in order to allow a flexible connection with a variety of anatomical sites, the elongated sections 840, 840' and connectors 842, 842' can be formed of a flexible material, as shown. However, in certain embodiments, a more rigid design may be selected based on the particular anatomic site and wound to be treated.

In various embodiments, the devices of the present disclosure can be used to treat wounds at numerous different anatomical sites. Further, although the devices are shown with one size, in various embodiments, the devices can be scaled based on the particular patient and anatomic site to be treated. In addition, although the devices are described for use with reduced pressure therapy, in various embodiments, the mechanical treatment devices of the present disclosure may be used alone, or without reduced pressure therapy systems, especially where it is desired to provide mechanical assistance for wound closure without penetrating skin or other tissue.

Other embodiments will be apparent to those skilled in the art from consideration of the specification and practice of the devices and methods disclosed herein.

What is claimed is:

1. A method for treating a wound, comprising:
   applying a sheet of flexible material around the entire perimeter of a wound;
   mechanically coupling two or more elongated sections to tissue at two or more locations around the wound, the two or more elongated sections being attached to a first body comprising at least one first opening configured for attachment to a reduced pressure source and at least one fluid passage extending at least partially through the first body and in fluid communication with the at least one opening;
   creating tension in the two or more elongated sections to pull the tissue at the two or more locations around the wound closer together; and
   activating a reduced pressure source to apply negative pressure to the fluid passage such that the negative pressure is transmitted to the wound beneath the sheet.

2. The method of claim 1, wherein each of the two or more elongated sections are flexible.

3. The method of claim 1, wherein mechanically coupling the two or more elongated sections to tissue comprises attaching the two or more elongated sections directly to tissue surrounding the wound.

4. The method of claim 1, wherein mechanically coupling the two or more elongated sections to tissue comprises attaching a flexible sheet to tissue surrounding the wound and attaching the two or more elongated sections to the sheet.

5. The method of any one of claims 3-4, wherein the two or more elongated sections are attached with an adhesive.

6. The method of claim 5, wherein the two or more elongated sections are attached without penetrating tissue.

7. The method of claim 1, wherein the two or more elongated sections include two elongated sections that extend in substantially opposite directions from the first body.

8. The method of claim 7, wherein each of the two or more elongated sections, comprise:
   a pair of substantially parallel elongated arms adjustably connected to the first body;
   a connector extending between a first end of the pair of elongated arms; and
   a handle region extending between second ends of the pair of elongated arms of each of the two elongated sections, wherein each pair of elongated arms extends from the first ends positioned on one side of the first body to the second ends positioned on an opposite site of the first body and the connectors of the two elongated sections are located on opposite sides of the first body.

9. The method of claim 8, wherein adjusting the length of the two or more elongated sections comprises applying force to handle regions extending between the second end of each pair of elongated arms of the two elongated sections to move the handle regions further apart from one another and move the connectors closer to one another.

10. The method of claim 9, further including engaging a locking mechanism to prevent movement of the connectors in at least one direction.

11. The method of claim 1, comprising:
    mechanically coupling six or more elongated sections to tissue at six or more locations around a wound; and
    creating tension in the six or more elongated sections to pull the tissue at the six or more locations around the wound closer together.

12. The method of claim 1, comprising:
    mechanically coupling four or more elongated sections to tissue at four or more locations around a wound; and creating tension in the four or more elongated sections to pull the tissue at the four or more locations around the wound closer together.

13. The method of claim 1, wherein attaching each of the two or more elongated sections to the first body comprises passing an end portion of each of the elongated sections into elongated section receiving portions of the first body.

14. The method of claim 13, wherein the elongated section receiving portions and the elongated sections form a locking mechanism such that the elongated sections can be passed into the elongated section receiving portions but cannot be pulled out of the elongated section receiving portions.

15. The method of claim 14, wherein the locking mechanism comprises a plurality of ridges positioned on a surface of each of the elongated sections.

16. The method of claim 1, wherein creating tension in the two or more elongated sections comprises rotating a rotatable portion of the first body to shorten the elongated sections.

17. The method of claim 16, further comprising engaging a locking mechanism configured to allow the rotatable portion to rotate in a first direction but not in a second direction opposite the first direction.

18. The method of claim 17, further comprising reversing the locking mechanism to allow the rotatable portion to rotate in the second direction but not in the first direction.

19. The method of claim 17, further comprising releasing the locking mechanism to allow the rotatable portion to rotate in the first direction and the second direction.

20. The method of claim 1, further comprising adjusting a position that one or more connectors are attached to the two or more elongated sections.

21. The method of claim 1, further comprising adjusting a length of one or more connectors attached to at least one of the elongated sections.

22. The method of claim 21, wherein adjusting the length of one or more connectors comprises adjusting a position of a tab portion of at least one of the connectors within a tab receiving portion of the connector to change the distance from the tab receiving portion to the end of an elongated section attached to the tab portion.

23. The method of claim 22, further comprising preventing the tab from moving out of the tab receiving portion.

24. The method of claim 1, further comprising positioning a flexible sheet over the wound to seal the wound.

25. The method of claim 24, wherein the sheet is positioned under the first body and the two or more elongated sections are mechanically coupled to a top surface of the sheet.

26. The method of claim 24, wherein the sheet is positioned on top of the first body and the two or more elongated sections are attached directly to the patient's tissue surrounding the wound.

27. The method of claim 24, further comprising attaching a reduced pressure therapy system to the first body to provide reduced pressure therapy to the wound.

28. The method of claim 27, further comprising placing a porous material body within the wound.

\* \* \* \* \*